United States Patent [19]

Yu

[11] 4,134,893

[45] Jan. 16, 1979

[54] COMPOUND 2[5-(4-CHLOROPHENYL)-2-FURANYL]-5-MERCAPTO-1,3,4-OXADIAZOLE POTASSIUM SALT IS USEFUL AS AN ANTIFUNGAL AGENT

[75] Inventor: Chia-Nien Yu, Norwich, N.Y.

[73] Assignee: Morton-Norwich Products, Inc., Norwich, N.Y.

[21] Appl. No.: 874,374

[22] Filed: Feb. 2, 1978

[51] Int. Cl.$^2$ ............................................ C07D 271/10
[52] U.S. Cl. ............................ 260/307 G; 260/307 A; 424/272
[58] Field of Search ......................... 260/307 G, 307 A

[56] References Cited

U.S. PATENT DOCUMENTS

| | | | |
|---|---|---|---|
| 2,918,473 | 12/1959 | Sherman | 260/307 |
| 3,202,673 | 8/1965 | Metivier et al. | 260/307 |
| 3,718,452 | 2/1973 | Dahle et al. | 71/92 |

Primary Examiner—Raymond V. Rush
Attorney, Agent, or Firm—Anthony J. Franze

[57] ABSTRACT

The compound 2-[5-(4-chlorophenyl)-2-furanyl]-5-mercapto-1,3,4-oxidiazole potassium salt is useful as an antifungal agent.

1 Claim, No Drawings

COMPOUND 2[5-(4-CHLOROPHENYL)-2-FURANYL]-5-MERCAPTO-1,3,4-OXADIAZOLE POTASSIUM SALT IS USEFUL AS AN ANTIFUNGAL AGENT

This invention is concerned with the chemical compound 2-[5-(4-chlorophenyl)-2-furanyl]-5-mercapto-1,3,4-oxadiazole potassium salt. This compound possesses antifungal activity and is useful in the prevention of fungal growth. In the commonly employed in vitro method for determining antifungal activity, concentrations of this compound ranging from 210–250 mcg/ml of test media inhibited the growth of *Candida albicans, Microsporum canis* and *Aspergillus niger.*

By virtue of its antifungal property, this compound is useful as an active ingredient in various compositons such as elixirs, sprays, dusts, unguents, solutions and the like designed for application to locales for the prevention and eradication of fungal growth.

In order that this invention may be readily available to and understood by those skilled in the art, the method currently preferred for its preparation is set forth below:

2-[5-(4-Chlorophenyl)-2-furanyl]-5-mercapto-1,3,4-oxadiazole potassium salt

To a solution of 14 g (0.25 mole) of potassium hydroxide in 3.5 l. of ethanol was added 59.25 g (0.25 mole) of 5-(4-chlorophenyl)-2- furoic acid hydrazide. Then 20 g (slight excess) of carbon disulfide was added. Solid separated quite readily. The mixture was heated at reflux overnight and a slightly cloudy solution was obtained. The mixture was filtered while still warm. The filtrate was cooled and solid separated. The solid was collected, washed with ethanol and air-dried to give 29 g (37%).

Anal. Calcd. for $C_{12}H_6ClKN_2O_2S$: C, 51.72%; H, 2.53%; N. 10.05%. Found: C, 51.93%; H, 2.62%; N, 9.90%.

What is claimed is:

1. The compound 2-[5-(4-chlorophenyl)-2-furanyl]-5-mercapto-1,3,4-oxadiazole potassium salt.